United States Patent [19]
Posedel

[11] Patent Number: 4,996,486
[45] Date of Patent: Feb. 26, 1991

[54] METHOD AND APPARATUS FOR INSPECTING LAMINATED IRON CORE STACKS FOR INTERLAMINATION SHORTS

[75] Inventor: Zlatimir Posedel, Neuenhof, Switzerland

[73] Assignee: Asea Brown Boveri Ltd., Baden, Switzerland

[21] Appl. No.: 358,638

[22] Filed: May 30, 1989

[30] Foreign Application Priority Data

May 30, 1988 [CH] Switzerland .................. 2043/88

[51] Int. Cl.$^5$ ............................................ G01R 31/06
[52] U.S. Cl. .................................... 324/545; 324/233;
324/242; 324/521; 324/529; 324/551; 324/559
[58] Field of Search ............... 324/521, 527, 528, 529,
324/545, 551, 554, 557, 559, 546, 547, 233, 228,
242, 220, 225; 320/99; 318/490; 340/648

[56] References Cited

U.S. PATENT DOCUMENTS

| 4,573,012 | 2/1986 | Bisson et al. | 324/225 X |
| 4,803,563 | 2/1989 | Dailey et al. | 324/220 X |
| 4,823,082 | 4/1989 | Nasu et al. | 324/233 X |

FOREIGN PATENT DOCUMENTS

| 0033802 | 8/1981 | European Pat. Off. |
| 0152687 | 8/1985 | European Pat. Off. |
| 0165761 | 12/1985 | European Pat. Off. |
| 2124952 | 9/1972 | France. |
| 2570501 | 3/1986 | France. |
| 1200146 | 7/1970 | United Kingdom. |

OTHER PUBLICATIONS

Elin–Zeitschrift (1984), No. ½ Von Schopper, E., pp. 53–62, "Das Elin–Diagnosesystem für Elektrische Grossmaschinen".
"El Cid Charts The Health of Large Machines," *Electrical Review International*, vol. 206, No. 11, 3/14/80, p. 54.

Primary Examiner—Reinhard J. Eisenzopf
Assistant Examiner—Robert W. Mueller
Attorney, Agent, or Firm—Oblon, Spivak, McClelland, Maier & Neustadt

[57] ABSTRACT

In order to detect interlamination shorts (8) in the case of laminated core stacks, the core stack (1) is magnetized with an auxiliary winding. The iron surface (15) is scanned with a measuring coil arrangement (5) comprising two electrically separated, mechanically interlinked coils (6, 7). The output signals from the coils are compared with each other in a downstream measuring instrument (9); in the case of an interlamination short, the fault current through the short-circuited laminations will induce in the coils different, phase-shifted voltages which make it possible to infer the position and size of the interlamination shorts.

7 Claims, 3 Drawing Sheets

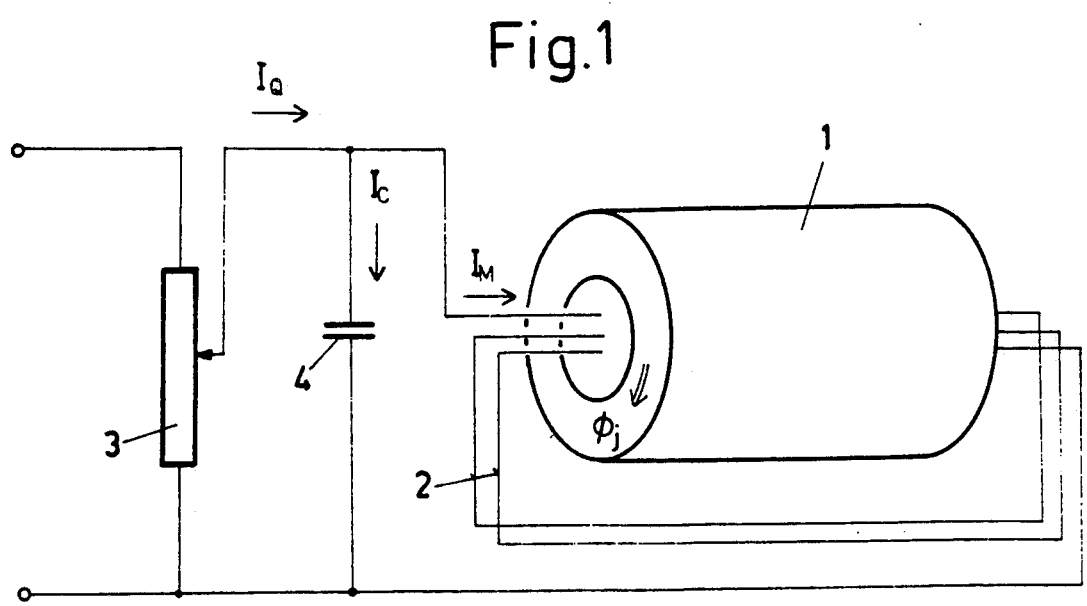
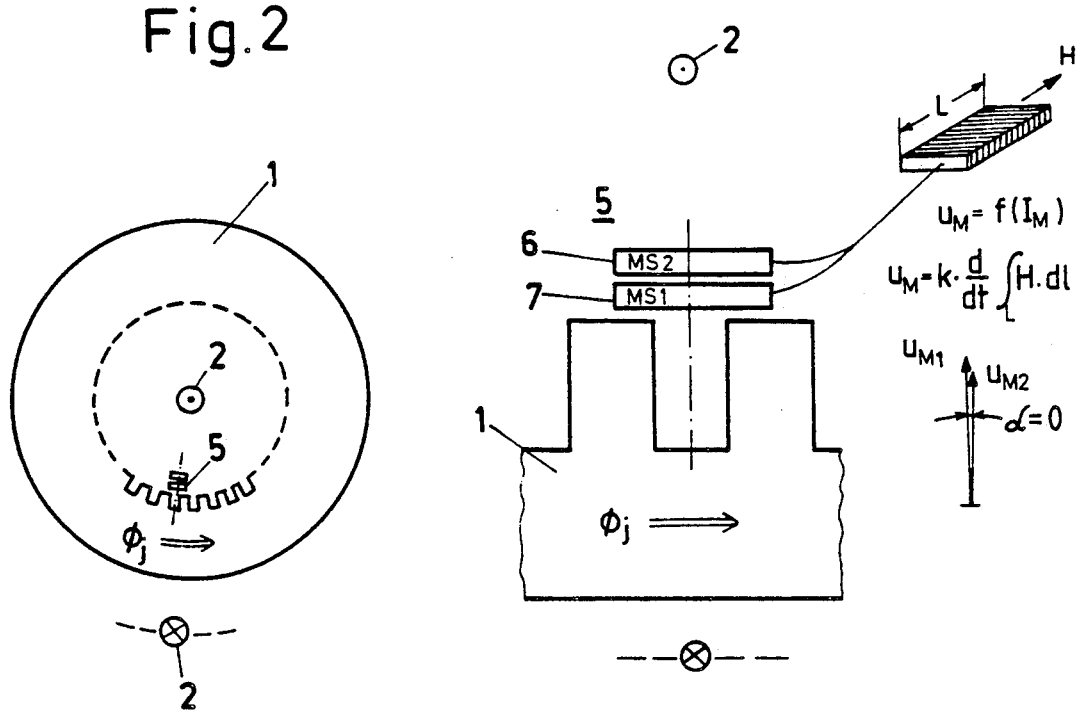

METHOD AND APPARATUS FOR INSPECTING LAMINATED IRON CORE STACKS FOR INTERLAMINATION SHORTS

BACKGROUND OF THE INVENTION

1. Field of the Invention

The invention relates to a method of inspecting laminated core stacks of electric machines for interlamination shorts, in which method the core stack is magnetized by means of an auxiliary winding and the iron surface is scanned by means of a measuring coil arrangement with downstream measuring instrument.

The invention relates furthermore to an apparatus for carrying out the method.

The starting point for the invention is a prior art as it emerges, for example, from the technical automobile journal "ELIN-Zeitschrift" 1984, No. ½, page 58, section entitled "Iron short separation of stator core stacks".

2. Discussion of Background

Laminated stator core bodies, in particular of electric machines, are inspected for interlamination shorts during manufacture and in operation in the course of maintenance operations using the measuring method comprising ring excitation of the stator lamination with rated induction. This method, which indicates the effect of currents due to interlamination shorts by local temperature differences, requires a high-power and regulable high-voltage source and excitation windings with large cross sections.

In the case of stator laminations with built-in winding rods, it is possible to detect only the locations of faults (short circuit of several laminations between each other) at the tooth surface and not the interlaminar faults in the slot bottom and at the slot sides with this inspection. This method detects only interlamination shorts having a particular contact resistance and resulting local temperature differences, and therefore does not detect all the interlamination short locations. The increase in temperature alone is insufficient to assess the interlamination short location quantitatively.

The disadvantages of the conventional iron lamination inspection can be avoided with the method disclosed in the journal "ELIN . . . " mentioned in the introduction of measuring current fields due to interlamination shorts with a weak yoke induction. Only a low-voltage supply connection is required to magnetize the core stack. Under these circumstances, virtually all interlamination shorts can be found, even those which are situated at the slot wall or in the slot bottom. It is also possible to determine the condition of the interlaminar insulation over the entire hole area (also slot area). The core stack can be inspected with a built-in rotor. The known method makes possible a qualified analysis of the interlamination short location. The efficiency of any stack repair carried out can easily be inspected immediately. In addition, the method makes it possible to compare the state of the core stacks of a plurality of machines. Changes in the core stack in the course of time and ageing processes can be detected.

A disadvantage in this case is that, in the case of a core stack fault location, the measured value reading read off at that point is proportional to the fault current ("cause") but not to the excess temperature ("effect") which occurs during operation. Since there is in fact a physical relationship, but not one which is simple to assign, between "cause" and "effect", the interpretation of the measurements requires some experience. In this connection, there is no problem in interpreting sharply defined measured value readings since such sharply defined measured valve readings are invariably due to faults; it is more difficult to interpret diffuse measurement readings since in this case these may be either "hot points" or inhomogeneities in the core stack.

In order to be able to assign measurement readings quantitatively to a wide variety of core stack types, a relative calibration is carried out at the start of every measurement. Small sub-areas of the core stack are superficially short circuited ("calibration fault location") with the excitation switched on and the measured value reading then recorded. A fault reading for an actual core stack fault then makes it possible to infer the actual size of the fault on the basis of the prior relative calibration.

SUMMARY OF THE INVENTION

Accordingly, one object of this invention is to provide a novel method for inspecting laminated iron core stacks for interlamination shorts, which method does not exhibit the disadvantages described and makes it possible to state the position and size of the damaged location quantitatively without having to carry out the relative calibrations on intact locations or calibration fault locations beforehand.

The object of the invention is furthermore to provide an apparatus for carrying out the method.

This object is achieved, according to the invention, by a method which comprises determining, by means of at least two electrically separated, radially spaced, but mechanically interlinked measuring coils, the radial distribution of the magnetic field of the current due to the interlamination short from the phase difference and/or the change in amplitude of the voltages induced in the measuring coils.

The associated apparatus for carrying out the method comprises an auxiliary coil for magnetizing the core stack, a measuring probe comprising two electrically separated, mechanically interlinked measuring coils, a measuring apparatus connected to the measuring coil for detecting the phase angle deviations and/or the changes in amplitude of the voltages induced in the measuring coils, and a downstream recording unit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows a basic diagram intended to show clearly the ring excitation of a stator core stack;

FIG. 2 shows a basic diagram intended to illustrate the position of the measuring coils;

FIG. 3 shows a section through the measuring arrangement at two stator teeth with associated phasor diagram with the core stack intact;

DESCRIPTION OF THE PREFERRED EMBODIMENTS

Figure 4:
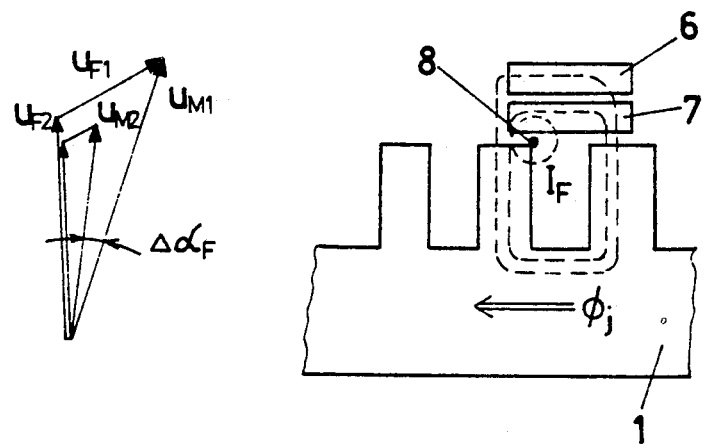
FIG. 4 shows an arrangement analogous to FIG. 3 with an interlamination short.

Referring now to the drawings, wherein like reference numerals designate identical or corresponding parts throughout the several views, in FIG. 1 a stator core stack 1 of an electric machine is weakly magnetized with a ring excitation as in the conventional measurement by means of a coil 2 placed round the stator core stack. In this measurement, the yoke induction is only approx. 5–10% of the rated induction. The low-voltage supply is sufficient to supply the induction coil. The ring magnetization is preferably carried out by means of an autotransformer 3 with adjustable output voltage (Variac) from the low-voltage supply. Compensating for the induced reactive current by means of a capacitor 4 connected in parallel makes it possible to reduce the supply current $I_Q$. In these measurements, the maximum supply current is approx. 20 A.

In contrast to the conventional iron lamination inspection with rated yoke induction, which inspection records the heating of the interlamination shorts ("hot spots")(infra-red camera, feeling by hand), this method determines, at the surface of the iron core stack, the radial distribution of the magnetic field of a current due to an interlamination short with a coil arrangement 5 comprising two measuring coils 6, 7 which are rigidly interlinked but are radially spaced from each other (FIGS. 2 and 3). The voltages $U_{M1}$, $U_{M2}$ measured at the ends of the measuring coils 6, 7 due to a core stack free of interlamination short are proportional to the magnetic potential between the coil ends or to the magnetizing current. The measuring coils consequently act as a magnetic volt meter ("Rogowski coil") for the line integral between the end points of the measuring coils. The angle between the induced measuring coil voltages is zero (FIG. 3). In the case of an interlamination short 8, the fault current $I_F$ will induce different, phase-shifted voltages in the measuring coils 6, 7 as a result of the short-circuited laminations.

$$U_F = \frac{w}{T} \cdot \int_L dl \frac{d}{dt} \cdot \iint_A \vec{B}_F \cdot dA$$

For the fault current, the measuring coils 6, 7 are induction coils which measure the magnetic inductions $B_F$ of the fault current which differ in the radial direction of the core stack. In the case of an interlamination short 8, this produces a phase shift $\Delta\alpha$ between the voltages of the measuring coils 6, 7 (phasor diagrams in FIGS. 4 and 5).

Figure 6:
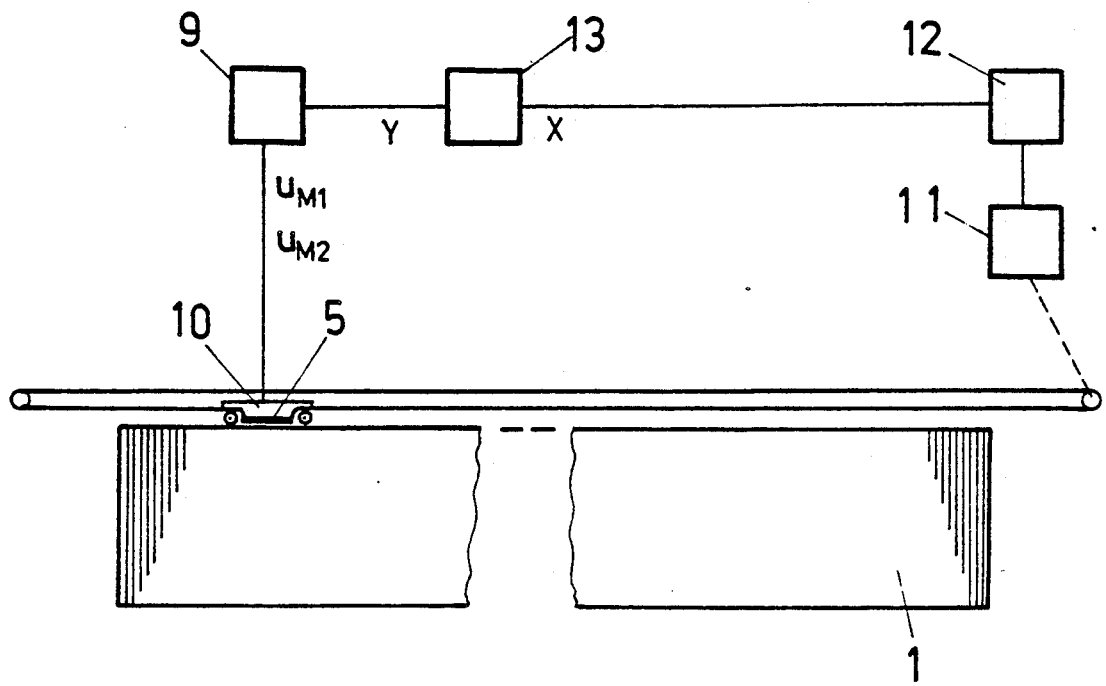
FIG. 6 shows a diagrammatic representation of the measuring arrangement together with a block circuit diagram thereof.

The phase shifts due to the fault current in the measured voltages depend on the size and the path length of the current interlamination due to interlamination short. The voltages from the measuring coils 6, 7 are amplified and the phase angle deviation $\Delta\alpha$ of the measured voltages and/or the amplitude change $\Delta\phi$ is determined by means of a phase detector 9 (FIG. 6).

The measuring coils 6, 7, which are preferably built into a mobile carriage 10, are moved by means of a cord drive and a drive motor 11 along the slots from one end to the other of the iron core stack 1. A rotation or displacement pickup coupled to the drive motor 11 makes it possible to detect the axial position of the carriage and consequently of the measuring coil arrangement 5.

The phase deviations $\Delta\alpha$ and/or amplitude changes $\Delta\phi$ in the measured voltages produced by the interlamination currents are recorded with an X-Y plotter 13 as a series of lines for each slot.

Figure 5:
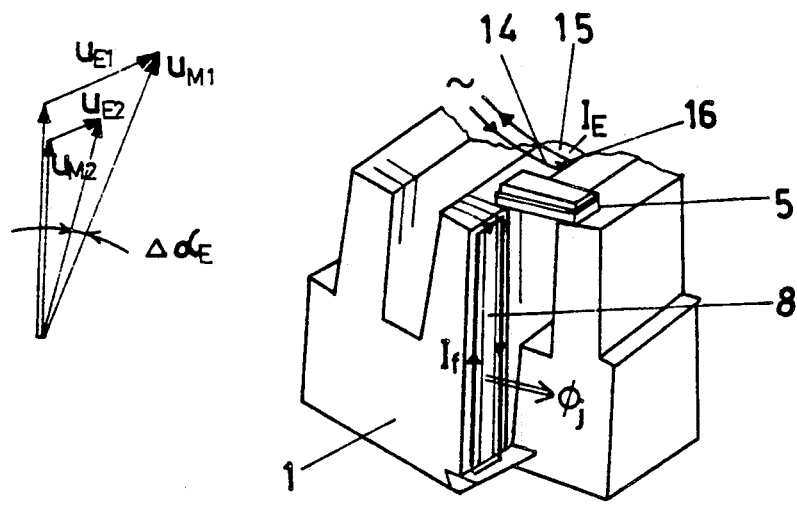
FIG. 5 shows an arrangement for producing reference signals with associated phasor diagram.

The signals recorded along the slots are compared with the signals which correspond to the currents due to the interlamination shorts. A loop 14 made of a thin conductor having the width of the interlamination short 16 is attached to the tooth surface 15 and fed with a current equivalent to the current due to the interlamination short (FIG. 5).

Figure 7:
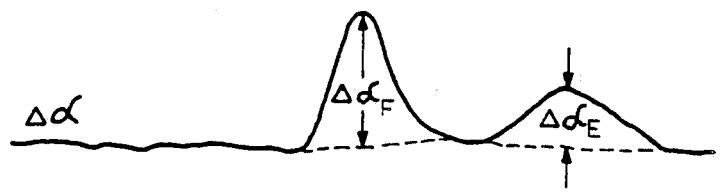
FIG. 7 shows a diagram which reproduces the variation in phase difference.

The current due to the interlamination short is fed in from the supply via the autotransformer 3. The currents due to interlamination shorts of short-circuited laminations are determined from the known voltage values between the laminations and the impedance of the individual laminations. The signal from the measuring coils ($\Delta\alpha$) is then recorded with and without this loop current ($\Delta\alpha_E$) and compared with the current due to the interlamination short ($\Delta\alpha_F$) (FIG. 7).

Instead of a cord drive, the carriage may also be constructed as a flat self-driven carriage mounting, its drive motor being coupled to a displacement or rotation pickup to determine the path travelled in accordance with FIG. 6.

The method described makes it possible to inspect a stator core stack in electric machines even with the rotor built in. In this case, the rotor has to be completely insulated with respect to ground on one side of the machine, which is standard in large generators.

A shaft not insulated on both sides of the machine would be like a secondarily short-circuited winding in which a few hundred amperes can flow in the case of weak excitation owing to the good magnetic coupling. An absence of shaft insulation on one side of the machine is noticeable as a result of the measurement of the shaft current with a Rogowski coil and the shaft voltage with respect to ground at the end of the machine on the non-drive side and as a result of the considerable increase in the ampere windings required to magnetize the stator stack.

The stator stack in machines with a rotor built in, in particular in the case of large turbine-driven machines, is therefore preferably magnetized from a high-current supply source which is connected to the insulated shaft between the two sides of the machine.

Obviously, numerous modifications and variations of the present invention are possible in the light of the above teachings. It is therefore to be understood that within the scope of the appended claims, the invention may be practiced otherwise than as specifically described herein.

What is claimed as new and desired to be secured by Letters Patent of the United States is:

1. A method of inspecting a laminated core stack of an electric machine for interlamination shorts, in which method the core stack is magnetized by means of an auxiliary winding and the laminated surface is scanned by means of a measuring coil arrangement with a downstream measuring instrument, which method comprises determining, by means of at least two electrically separated, radially spaced, but mechanically interlinked measuring coils of said measuring coil arrangement, the radial distribution of the magnetic field of the current ($I_F$) due to the interlamination short from at least on of the phase difference and the change in amplitude of the voltages ($U_{M1}$, $U_{M2}$) induced in the at least two measuring coils.

2. The method as claimed in claim 1, wherein the phase deviation ($\Delta\alpha$) of the signals from the measuring coils is determined by means of a phase detector.

3. The method as claimed in claim 1, wherein the difference in amplitude ($\Delta\phi$) of the signals from the measuring coils is detected with a recording instrument.

4. The method as claimed in one of claims 1-3, wherein the signals recorded are compared with known values which correspond to currents produced by interlamination shorts, a loop with equivalent width being attached to the surface of the iron core and being fed with a known current corresponding to an interlamination short.

5. The method as claimed in one of claims 1-3, wherein the measuring coils are arranged on a carriage and are moved across the core stack from one end to the other by means of a drive motor.

6. The method as claimed in one of claims 1-3, wherein the core stack is magnetized via the rotor shaft from a high-current supply source which is connected to the insulated shaft between the two sides of the machine.

7. An apparatus for carrying out the method of inspecting a laminated core stack of an electric machine for interlamination shorts, wherein the core stack is magnetized by means of an auxiliary winding and the laminated surface is scanned by means of a measuring coil arrangement with a downstream measuring instrument, said apparatus comprising an auxiliary coil for magnetizing the core stack, said measuring coil apparatus comprising, at least two electrically separated, radially spaced, but mechanically interlinked measuring coils, which are used to determine the radial distribution of the magnetic field of the current ($I_F$) due to the interlamination short from at least on of the phase difference and the change in amplitude of the voltage ($U_{M1}$, $U_{M2}$) induced in the at least two measuring coils, measuring means connected to the measuring coils for detecting at least one of the phase angle deviation and the changes in amplitude of the voltages ($U_{M1}$, $U_{M2}$) induced in the measuring coils, and a recording unit connected to the measuring means.

* * * * *